United States Patent [19]

Antos

[11] 4,333,856
[45] * Jun. 8, 1982

[54] HYDROCARBON ISOMERIZATION CATALYST AND PROCESS

[75] Inventor: George J. Antos, Bartlett, Ill.

[73] Assignee: UOP Inc., Des Plaines, Ill.

[*] Notice: The portion of the term of this patent subsequent to Jul. 23, 1998, has been disclaimed.

[21] Appl. No.: 212,641

[22] Filed: Dec. 3, 1980

Related U.S. Application Data

[63] Continuation-in-part of Ser. No. 68,278, Aug. 20, 1979, Pat. No. 4,256,566, which is a continuation-in-part of Ser. No. 833,332, Sep. 14, 1977, Pat. No. 4,165,276.

[51] Int. Cl.³ .................... B01J 27/08; B01J 27/10
[52] U.S. Cl. .................... 252/441; 252/442; 585/482; 585/669; 585/747; 585/748; 585/374
[58] Field of Search .................... 252/441, 442

[56] References Cited

U.S. PATENT DOCUMENTS 3,790,473  2/1974  Rausch .................... 252/441 X

Primary Examiner—Patrick Garvin
Attorney, Agent, or Firm—James R. Hoatson, Jr.; John G. Cutts, Jr.; William H. Page, II

[57] ABSTRACT

Isomerizable hydrocarbons are isomerized using a catalytic composite comprising a combination of a catalytically effective amount of a pyrolyzed rhenium carbonyl component with a porous carrier material containing a uniform dispersion of catalytically effective amounts of a platinum group component, which is maintained in the elemental metallic state during the incorporation and pyrolysis of the rhenium carbonyl component, of a tin component, and of a halogen component and from about 1 to about 100 weight percent of a Friedel-Crafts metal halide calculated on a Friedel-Crafts metal halide-free basis.

8 Claims, No Drawings

HYDROCARBON ISOMERIZATION CATALYST AND PROCESS

CROSS-REFERENCE TO RELATED APPLICATIONS

This application is a continuation-in-part of my co-pending application Ser. No. 68,278 filed Aug. 20, 1979 and issued as a U.S. Pat. No. 4,256,566 on Mar. 17, 1981, which is a continuation-in-part of my application Ser. No. 833,332 filed September 14, 1977 now U.S. Pat. No. 4,165,276. The teachings of which applications are incorporated herein by specific reference thereto.

FIELD OF THE INVENTION

This invention relates to a catalyst and process for isomerizing isomerizable hydrocarbons including isomerizable paraffins, cycloparaffins, olefins and alkylaromatics. More particularly, this invention relates to a process for isomerizing isomerizable hydrocarbons with a catalyst comprising a combination of a catalytically effective amount of a pyrolyzed rhenium carbonyl component with a porous carrier material containing a uniform dispersion of catalytically effective amounts of a platinum group component, which is maintained in the elemental metallic state during the incorporation and pyrolysis of the rhenium carbonyl component, of a tin component, and of a halogen component. The present invention uses a dual-function catalyst having both a hydrogenation-dehydrogenation function and a cracking function which affords substantial improvements in hydrocarbon isomerization processes that have traditionally used dual-function catalysts.

Processes for the isomerization of hydrocarbons have aquired significant importance within the petrochemical and petroleum refining industry. The demand for para-xylene has created a demand for processes to isomerize other xylene isomers and ehtylbenzene to produce para-xylene. The demand for certain branched chain paraffins, such as isobutane or isopentane, as intermediates in producing high octane motor fuel alkylate, can be met by isomerizing the corresponding normal paraffins. It is desired that the alkylate be highly branched to provide a high octane rating. This can be accomplished by alkylating an isoparaffin with $C_4$–$C_7$ internal olefins which, in turn, can be produced by isomerization of corresponding linear alphaolefins.

Catalytic composites exhibiting a dual hydrogenation-dehydrogenation and cracking function are widely used in the petroleum and petrochemical industry to isomerize hydrocarbons. Such catalysts generally have a heavy metal component, e.g., metals or metallic compounds of Groups V through VIII of the Periodic Table, to impart a hydrogenation-dehydrogenation function, with an acid-acting inorganic oxide to impart a cracking function. In catalysis of isomerization reactions, it is important that the catalytic composite not only catalyze the specific desired isomerization reaction by having its dual hydrogention-dehydrogenation function correctly balanced against its cracking function, but also that the catalyst perform its desired functions well over prolonged periods of time.

The performance of a given catalyst in a hydrocarbon isomerization process is typically measured by the activity, selectivity, and stability of the catalyst. Activity refers to the ability of a catalyst to isomerize the hydrocarbon reactants into the corresponding isomers at a specified set of reaction conditions; selectivity refers to the percent of reactants isomerized to form the desired isomerized product and/or products; stability refers to the rate of change of the selectivity and activity of the catalyst.

The principal cause of instability (i.e., loss of selectivity and activity in an originally selective, active catalyst) is the formation of coke on the catalytic surface of the catalyst during the reaction. This coke is characterizable as a high molecular weight, hydrogen-deficient, carbonaceous material, typically having an atomic carbon to hydrogen ratio of about 1 or more. Thus, a problem in the hydrocarbon isomerization art is the development of more active and selective composites not sensitive to the carbonaceous materials and/or having the ability to suppress the rate of formation of these carbonaceous materials on the catalyst. A primary aim of the art is to develop a hydrocarbon isomerization process utilizing a dual-function catalyst having superior activity, selectivity and stability. In particular, it is desired to provide a process wherein hydrocarbons are isomerized without excess cracking or other decomposition reactions which lower the overall yield of the process and make it more difficult to operate.

SUMMARY OF THE INVENTION

It is an object of this invention to provide a process for isomerizing isomerizable hydrocarbons. It is another object of this invention to provide an isomerization process using a particular isomerization catalyst effective in isomerizing isomerizable hydrocarbons without introducing undesired decomposition and/or cracking reactions. It is a further object of this invention to provide a process for isomerizing isomerizable hydrocarbons utilizing a dual-function catalyst having superior activity, selectivity and stability.

It is also an object of the present invention to provide an improved isomerization catalyst.

Accordingly, the present invention provides a catalyst comprising a combination of a catalytically effective amount of a pyrolyzed rhenium carbonyl component with a porous carrier material containing a uniform dispersion of catalytically effective amounts of a platinum group component, which is maintained in the elemental metallic state during the incorporation and pyrolysis of the rhenium carbonyl component, of a tin component, of a halogen component and of about 1 to about 100 wt.% of a Friedel-Crafts metal halide calculated on a Friedel-Crafts metal halide free basis.

In another embodiment, the present invention provides a process for isomerizing an isomerizable hydrocarbon which comprises contacting said hydrocarbon at isomerization conditions with a catalyst comprising a combination of a catalytically effective amount of a pyrolyzed rhenium carbonyl component with a porous carrier material containing a uniform dispersion of catalytically effective amounts of a platinum group component, which is maintained in the elemental metallic state during the incorporation and pyrolysis of the rhenium carbonyl component, of a tin component, and of a halogen component.

DETAILED DESCRIPTION

The process of this invention is applicable to the isomerization of isomerizable saturated hydrocarbons including acyclic paraffins and naphthenes and is particularly suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those containing at least 5 carbon atoms in the ring such as alkylcyclopentanes and cyclohexanes, including methylcyclopentane, dimethylcyclopentane, cyclohexane, methylcyclohexane, dimethylcyclohexane, etc. This process also applies to the conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions and mixtures thereof. It is not intended, however, to limit this invention to these enumerated saturated hydrocarbons and it is contemplated that straight or branched chain saturated hydrocarbons and naphthenes containing up to about 20 carbon atoms per molecule may be isomerized according to the process of the present invention with $C_4$–$C_9$ acyclic saturated hydrocarbons and $C_5$–$C_9$ cycloparaffins being particularly preferred.

The olefins applicable within this isomerization process are generally a mixture of olefinic hydrocarbons of approximately the same molecular weight, including the 1-isomer, 2-isomer and other position isomers, capable of undergoing isomerization to an olefin in which the double bond occupies a different position in the hydrocarbon chain. The process of this invention can be used to provide an olefinic feedstock for motor fuel alkylation purposes containing an optimum amount of the more centrally located double bond isomers, by converting the 1-isomer, or other near-terminal-position isomer into olefins wherein the double bond is more centrally located in the carbon atom chain. The process of this invention is applicable to the isomerization of such isomerizable olefinic hydrocarbons as 1-butene to 2-butene or 3-methyl-1-butene to 2-methyl-2-butene. The process of this invention can be utilized to shift the double bond of an olefinic hydrocarbon such as 1-pentene, 1-hexene, 2-hexene, or 4-methyl-1-pentene to a more centrally located position so that 2-pentene, 2-hexene, 3-hexene or 4-methyl-2-pentene, respectively, can be obtained. It is not intended to limit this invention to the enumerated olefinic hydrocarbons. It is contemplated that shifting the double bond to a different position may be effective in straight or branched chain olefinic hydrocarbons containing from 4 up to about 20 carbon atoms per molecule. The process of this invention also applies to the hydroIsomerization of olefins wherein olefins are converted to branched-chain paraffins and/or branched olefins.

The process of this invention is also applicable to the isomerization of isomerizable alkylaromatic hydrocarbons, e.g., ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the alkylbenzene hydrocarbons, particularly the $C_8$ alkylbenzenes, and non-equilibrium mixtures of various $C_8$ aromatic isomers. Higher molecular weight alkylaromatic hydrocarbons such as the alkylnaphthalenes, the alkylanthracenes, the alkylphenanthrenes, etc., are also suitable.

The isomerizable hydrocarbons may be utilized as found in selective fractions from various naturally-occuring petroleum streams, e.g., as individual components or as certain boiling range fractions obtained by the selective fractionation and distillation of catalytically cracked gas oil. The process of this invention may be utilized for complete conversion of isomerizable hydrocarbons when they are present in minor quantities in various fluid or gaseous streams. The isomerizable hydrocarbons for use in the process of this invention need not be concentrated. For example, isomerizable hydrocarbons appear in minor quantities in various refinery offstreams, usually diluted with gases such as hydrogen, nitrogen, methane, ethane, propane, etc. These offstreams, containing minor quantities of isomerizable hydrocarbons, are obtained from various refinery installations, including thermal cracking units, catalytic cracking units, thermal reforming units, coking units, polymerization units, dehydrogenation units, etc., and have in the past been burned as fuel, since an economical process for the utilization of the hydrocarbon content has not been available. This is particularly true of refinery fluid streams which contain minor quantities of isomerizable hydrocarbons. The process of this invention allows the isomerization of aromatic streams such as reformate to produce xylenes, particularly para-xylene, thus upgrading the reformate from its gasoline value to a high petrochemical value.

As hereinbefore indicated, the catalyst utilized in the process of the present invention comprises a combination of a catalytically effective amount of a pyrolyzed rhenium carbonyl component with a porous carrier material containing a uniform dispersion of catalytically effective amounts of a platinum group component, which is maintained in the elemental metallic state during the incorporation and pyrolysis of the rhenium carbonyl component, of a tin component, and of a halogen component.

Considering first the porous carrier material utilized in the present invention, it is preferred that the material be a porous, adsorptive, high-surface area support having a surface area of about 25 to about 500 $m^2/g$. The porous carrier material should be relatively refractory to the conditions utilized in the isomerization process, and it is intended to include within the scope of the present invention carrier materials which have traditionally been utilized in dual-function hydrocarbon conversion catalysts such as: (1) activated carbon, coke or charcoal; (2) silica or silica gel, silicon carbide, clays and silicates including these synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$ and other like compounds having the formula $MO \cdot Al_2O_3$, where M is a metal having a valence of 2; and, (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportions of other well-known refractory inorganic oxides such as silica, zirconia, magnesia, etc.; however, the preferred support is substantially pure gamma- or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 m$^2$/g. In general, best results are typically obtained with a gamma-alumina carrier material which is used in the form of spherical particles having: a relatively small diameter (i.e., typically about 1/16-inch), an apparent bulk density of about 0.3 to about 0.8 g/cc, a pore volume of about 0.4 ml/g and a surface area of about 200 m$^2$/g.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere; and alumina spheres may be continuously manufactured by the well-known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammonical solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

Another particularly preferred alumina carrier material is synthesized from a unique crystalline alumina powder which has been characterized in U.S. Pat. Nos. 3,852,190 and 4,012,313 as a byproduct from a Ziegler higher alcohol synthesis reaction as described in Ziegler's U.S. Pat. No. 2,892,858. For purposes of simplification, the name "Ziegler alumina" is used herein to identify this material. It is presently available from the Conoco Chemical Division of Continental Oil Company under the trademark Catapal. This material is an extremely high purity alpha-alumina monohydrate (boehmite) which after calcination at a high temperature has been shown to yield a high purity gamma-alumina. It is commercially available in three forms: (1) Catapal SB—a spray dried powder having a typical surface area of 250 m$^2$/g; (2) Catapal NG—a rotary kiln dried alumina having a typical surface area of 180 m$^2$/g; and (3) Dispal M—a finely divided dispersible product having a typical surface area of about 185 m$^2$/g. For purposes of the present invention, the preferred starting material is the spray dried powder, Catapal SB. This alpha-alumina monohydrate powder may be formed into a suitable catalyst material according to any of the techniques known to those skilled in the catalyst carrier material forming art. Spherical carrier material particles can be formed, for example, from this Ziegler alumina by: (1) converting the alpha-alumina monohydrate powder into an alumina sol by reaction with a suitable peptizing agent and water and thereafter dropping a mixture of the resulting sol and a gelling agent into an oil bath to form spherical particles of an alumina gel which are easily converted to a gamma-alumina carrier material by known methods; (2) forming an extrudate from the powder by established methods and thereafter rolling the extrudate particles on a spinning disc until spherical particles are formed which can then be dried and calcined to form the desired particles of spherical carrier material; and (3) wetting the powder with a suitable peptizing agent and thereafter rolling particles of the powder into spherical masses of the desired size in much the same way that children have been known to make parts of snowmen by rolling snowballs down hills covered with wet snow. This alumina powder can also be formed in any other desired shape or type of carrier material known to those skilled in the art such as rods, pills, pellets, tablets, granules, extrudates and the like forms by methods well known to the practitioners of the catalyst carrier material forming art. A preferred type of carrier material for the present invention is a cylindrical extrudate having a diameter of about 1/32" to about 1/8" (especially about 1/16") and a length to diameter (L/D) ratio of about 1:1 to about 5:1, with an L/D ratio of about 2:1 being especially preferred. The especially preferred extrudate form of the carrier material is preferably prepared by mixing the alumina powder with water and a suitable peptizing agent such as nitric acid, acetic acid, aluminum nitrate and the like material unitl an extrudable dough is formed. The amount of water added to form the dough is typically sufficient to give a loss of ignition (LOI) at 500° C. of about 45 to 65 wt.%, with a value of about 55 wt.% being especially preferred. On the other hand, the acid addition rate is generally sufficient to provide about 2 to 7 wt.% of the volatile free alumina powder used in the mix, with a value of about 3 to 4 wt.% being especially preferred. The resulting dough is then extruded through a suitably sized die to form extrudate particles. These particles are then dried at a temperature of about 500° F. to 800° F. for a period of about 0.1 to about 5 hours and thereafter calcined at a temperature of about 900° F. to about 1500° F. for a period of about 0.5 to about 5 hours to form the preferred extrudate particles of the Ziegler alumina carrier material. In addition, in some embodiments of the present invention the Ziegler alumina carrier material may contain minor proportions of other well-known refractory inorganic oxides such as silica, titanium dioxide, zirconium dioxide, chromium oxide, beryllium oxide, vanadium oxide, cesium oxide, hafnium oxide, zinc oxide, iron oxide, cobalt oxide, magnesia, boria, thoria, and the like materials which can be blended into the extrudable dough prior to the extrusion of same. In the same manner crystalline zeolitic aluminosilicates such as naturally occurring or synthetically prepared mordenite and/or faujasite, either in the hydrogen form or in a form which has been treated with a multivalent cation, such as a rare earth, can be incorporated into this carrier material by blending finely divided particles of same into the extrudable dough prior to extrusion of same. A preferred carrier material of this type is substantially pure Ziegler alumina having an apparent bulk density (ABD) of about 0.6 to 1 g/cc (especially an ABD of about 0.7 to about 0.85 g/cc), a surface area (B.E.T.) of about 150 to about 280 m$^2$/g (preferably about 185 to about 235 m$^2$/g) and a pore volume (B.E.T.) of about 0.3 to about 0.8 cc/g.

A first essential ingredient of the subject catalyst is the platinum group component. That is, it is intended to cover the use of platinum, iridium, osmium, ruthenium, rhodium, palladium, or mixtures thereof as a first component of the attenuated superactive catalytic composite. It is an essential feature of the present invention that substantially all of this platinum group component is uniformly dispersed throughout the porous carrier material in the elemental metallic state prior to the incorporation of the rhenium carbonyl ingredient. Generally, the amount of this component present in the form of catalytic composites is small and typically will comprise about 0.01 to about 2 wt.% of the final catalytic composite, calculated on an elemental basis. Excellent results are obtained when the catalyst contains about 0.05 to about 1 wt.% of platinum, iridium, rhodium, palladium or ruthenium metal. Particularly preferred mixtures of these platinum group metals preferred for use in the composite of the present invention are: (1) platinum and iridium, (2) platinum and rhodium, and (3) platinum and ruthenium.

This platinum group component may be incorporated into the porous carrier material in any suitable manner known to result in a relatively uniform distribution of this component in the carrier material such as coprecipitation or cogelation, ion-exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other water-soluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlorohodate (III), sodium hexanitrohordate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium, or palladium chloride compound, such as chloroplatinic, chloroiridic, or chloropalladic acid or rhodium trichloride hydrate, is preferred since it facilitates the incorporation of both the platinum group component and at least a minor quantity of the preferred halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum group compound.

A second essential constituent of the multimetallic catalyst of the present invention is a tin component. This component may in general be present in the instant catalytic composite in any catalytically available form such as the elemental metal, a compound like the oxide, hydroxide, halide, oxyhalide, aluminate, or in chemical combination with one or more of the other ingredients of the catalyst. Although it is not intended to restrict the present invention by this explanation, it is believed that best results are obtained when the tin component is present in the composite in a form wherein substantially all of the tin moiety is in an oxidation state above that of the elemental metal such as in the form of tin oxide or tin halide or tin oxyhalide or a mixture thereof and the subsequently described oxidation and reduction steps that are preferably used in the preparation of the instant catalytic composite are specifically designed to achieve this end. The term "tin-oxyhalide" as used herein refers to a coordinated complex of tin, oxygen and halogen which are not necessarily present in the same relationship for all cases covered herein. This tin component can be used in any amount which is catalytically effective, with good results obtained, on an elemental basis, with about 0.005 to about 5 wt.% tin in the catalyst. Best results are ordinarily achieved with about 0.01 to about 1 wt.% tin, calculated on an elemental basis. The preferred atomic ratio of tin to platinum group metal for this catalyst is about 0.1:1 to about 13:1.

This tin component may be incorporated in the catalytic composite in any suitable manner known to the art to result in a relatively uniform dispersion of the tin moiety in the carrier material, such as by coprecipitation or cogelation or coextrusion with the porous carrier material, ion exchange with the gelled carrier material, or impregnation of the porous carrier material either after, before, or during the period when it is dried and calcined. It is to be noted that it is intended to include within the scope of the present invention all conventional methods for incorporating and simultaneously uniformly distributing a metallic component in a catalytic composite and the particular method of incorporation used is not deemed to be an essential feature of the present invention. One particularly preferred method of incorporating the tin component into the catalytic composite involves cogelling or coprecipitating the tin component in the form of the corresponding hydrous oxide during the preparation of the preferred carrier material, alumina. This method typically involves the addition of a suitable sol-soluble or sol-dispersible tin compound such as stannic or stannous chloride, tin acetate, and the like to the alumina hydrosol, thoroughly mixing the resulting tin-containing hydrosol in order to uniformly disperse the tin moiety throughout the sol, and then combining the tin-containing hydrosol with a suitable gelling agent and dropping the resulting mixture into an oil bath, etc., as explained in detail hereinbefore. Alternatively, the tin compound can be added to the gelling agent. After drying and calcining the resulting gelled carrier material in air, there is obtained an intimate combination of alumina and tin oxide and/or oxyhalide. A second preferred method of incorporating the tin component into the catalytic composite involves utilization of a soluble, decomposable compound of tin to impregnate the porous carrier material. In general, the solvent used in this impregnation step is selected on the basis of the capability to dissolve the desired tin compound and to hold it in solution until it is evenly distributed throughout the carrier material without adversely affecting the carrier material or the other ingredients of the catalyst—for example, a suitable alcohol, ether, acid and the like solvents. The solvent is preferably an aqueous, acidic solution. The tin component may thus be added to the carrier material by commingling the latter with an aqueous acidic solution of suitable tin salt, complex, or compound such as stannic acetate, stannous or stannic bromide, stannous or stannic chloride, stannic chloride pentahydrate, stannic chloride diamine, stannic trichloride bromide, stannic chromate, stannous or stannic fluoride, stannic tartrate, dimethyltin dibromide, dimethyltin dichloride, ethylpropyltin dichloride, triethyltin hydroxide, trimethyltin chloride, and the like compounds. A particularly preferred impregnation solution comprises an acidic aqueous solution of stannic or stannous chloride. Suitable acids for use in the impregnation solution are: inorganic acids such as hydrochloric acid, nitric acid, and the like, and strongly acidic organic acids such as oxalic acid, malonic acid, citric acid, and the like. In general, the tin component can be impregnated either prior to, simultaneously with, or after the platinum group component is added to the carrier material. However, excellent results are obtained when the tin component is incorporated into the carrier material during its preparation and thereafter the platinum group component is added in a subsequent impregnation step after the tin-containing carrier material is calcined. A third preferred method of adding the tin component is to select a rhenium-carbonyl complex that also contains a tin ligand in the subsequently described rhenium-carbonyl incorporation step, thereby adding the tin component simultaneously with the rhenium-carbonyl component.

It is especially preferred to incorporate a halogen component into the platinum group metal-containing porous carrier material prior to the reactions thereof with the rhenium carbonyl reagent. Although the precise form of the chemistry of the association of the halogen component with the catalytic composite is not entirely known, it is customary in the art to refer to the halogen component as being chemically combined with the carrier material or with the platinum group and/or tin components in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or during or after the addition of the platinum group and tin components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group and/or tin components, for example, through the utilization of a mixture of chloroplatinic acid and hydrogen chloride. In another situation, the alumina hydrosol which is typically utilized to form a preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5%, by weight of halogen, calculated on an elemental basis. In isomerization or hydrocracking embodiments, it is generally preferred to utilize relatively larger amounts of halogen in the catalyst—typically, ranging up to about 10 wt.% halogen calculated on an elemental basis, and more preferably, about 1 to about 5 wt.%. It is to be understood that the specified level of halogen component in the instant attenuated superactive catalyst can be achieved or maintained during use in the conversion of hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm. of the hydrocarbon feed, and preferably about 1 to 10 wt. ppm.

After the tin components (when added prior to the rhenium carbonyl incorporation step) and platinum group components are combined with the porous carrier material, the resulting platinum group metal- and tin-containing carrier material will generally be dried at a temperature of about 200° F. to about 600° F. for a period of typically about 1 to about 24 hours or more and thereafter oxidized at a temperature of about 700° F. to about 1100° F. in air or oxygen atmosphere for a period of about 0.5 to about 10 or more hours or converts substantially all of the platinum group and tin components to the corresponding metallic oxides. When the preferred halogen component is utilized in the present composition, best results are generally obtained when the halogen content of the platinum group metal- and tin-containing carrier material is adjusted during this oxidation step by including a halogen or a halogen-containing compound in the air or oxygen atmosphere utilized. For purposes of the present invention, the particularly preferred halogen is chlorine and it is highly recommended that the halogen compound utilized in this halogenation step be either hydrochloric acid or a hydrochloric acid-producing substance. In particular, when the halogen component of the catalyst is chlorine, it is preferred to use a molar ratio of $H_2O$ to HCl of about 5:1 to about 100:1 during at least a portion of this oxidation step in order to adjust the final chlorine content of the catalyst to a range of about 0.1 to about 3.5 wt.%. Preferably, the duration of this halogenation step is about 1 to 5 or more hours.

A crucial feature of the present invention involves subjecting the resulting oxidized, tin-containing (when added prior to the rhenium carbonyl incorporation step) and platinum group metal-containing, and typically halogen-treated, carrier material to a substantially water-free reduction step before the incorporation of the rhenium component by means of the rhenium carbonyl reagent. The importance of this reduction step comes from my observation that when an attempt is made to prepare the instant catalytic composite without first reducing the platinum group component, no significant improvement in the platinum-rhenium-tin catalyst system is obtained; put another way, it is my finding that it is essential for the platinum group component to be well dispersed in the porous carrier material in the elemental metallic state prior to incorporation of the rhenium component by the unique procedure of the present invention in order for synergistic interaction of the rhenium carbonyl with the dispersed platinum group metal to occur according to the theories that I have previously explained. Accordingly, this reduction step is designed to reduce substantially all of the platinum group component to the elemental metallic state and to assure a relatively uniform and finely divided dispersion of this metallic component throughout the porous carrier material. Preferably a substantially pure and dry hydrogen stream (by the use of the word "dry", I mean that it contains less than 20 vol. ppm. water and preferably less than 5 vol. ppm. water) is used as the reducing agent in this step. The reducing agent is contacted with the oxidized, platinum group metal- and tin-containing carrier material at conditions including a reduction temperature of about 450° F. to about 1200° F., a gas hourly space velocity (GHSV) sufficient to rapidly dissipate any local concentrations of water formed during the reduction of the platinum group metal oxide, and a period of about 0.5 to about 10 or more hours selected to reduce substantially all of the platinum group component to the elemental metallic state. Once this condition of finely divided dispersed platinum group metal in the porous carrier material is achieved, it is important that environments and/or conditions that could disturb or change this condition be avoided; specifically, I much prefer to maintain the freshly reduced carrier material containing the platinum group metal under a blanket of inert gas to avoid any possibility of contamination of same either by water or by oxygen.

A third essential ingredient of the present attenuated superactive catalytic composite is a rhenium component which I have chosen to characterize as a pyrolyzed rhenium carbonyl component in order to emphasize that the rhenium moiety of interest in my invention is the rhenium produced by decomposing a rhenium carbonyl in the presence of a finely divided dispersion of a platinum group metal and in the absence of materials such as oxygen or water which could interfere with the basic desired interaction of the rhenium carbonyl component with the platinum group metal component as previously explained. In view of the fact that all of the rhenium contained in a rhenium carbonyl complex is present in the elemental metallic state, an essential requirement of my invention is that the resulting reaction product of the rhenium carbonyl complex with the platinum group metal-containing carrier material is not subjected to conditions which could in any way interfere with the maintenance of the rhenium moiety in the elemental metallic state; consequently, avoidance of any conditions which would tend to cause the oxidation of any portion of the rhenium ingredient or of the platinum group ingredient is a requirement for full realization of the synergistic interaction enabled by the present invention. This rhenium component may be utilized in the resulting composite in any amount that is catalytically effective with the preferred amount typically corresponding to about 0.01 to about 5 wt.% thereof, calculated on an elemental rhenium basis. Best results are ordinarily obtained with about 0.05 to about 1 wt.% rhenium. The traditional rule for rhenium-platinum catalyst system is that best results are achieved when the amount of the rhenium component is set as a function of the amount of the platinum group component also hold for my composition; specifically, I find that best results with a rhenium to platinum group metal atomic ratio of about 0.1:1 to about 10:1, with an especially useful range comprising about 0.2:1 to about 5:1 and with superior results achieved at an atomic ratio of rhenium to platinum group metal of about 1:1 to about 3:1.

The rhenium carbonyl ingredient may be reacted with the reduced platinum group metal-containing porous carrier material in any suitable manner known to those skilled in the catalyst formulation art which results in relatively good contact between the rhenium carbonyl complex and the platinum group component contained in the porous carrier material. One acceptable procedure for incorporating the rhenium carbonyl component into the composite involves sublimating the rhenium carbonyl complex under conditions which enable it to pass into the vapor phase without being decomposed and thereafter contacting the resulting rhenium carbonyl sublimate with the platinum group metal-containing porous carrier material under conditions designed to achieve intimate contact of the carbonyl reagent with the platinum group metal dispersed on the carrier material. Typically this procedure is preformed under vacuum at a temperature of about 70° F. to about 250° F. for a period of time sufficient to react the desired amount of rhenium with the carrier material. In some cases, an inert carrier gas such as nitrogen can be admixed with the rhenium carbonyl sublimate in order to facilitate the intimate contacting of same with the platinum group metal-loaded porous carrier material. A particularly preferred way of accomplishing this rhenium carbonyl reaction step is an impregnation procedure wherein the platinum metal-containing porous carrier material is impregnated with a suitable solution containing the desired quantity of the rhenium carbonyl complex. For purposes of the present invention, organic solutions are preferred, although any suitable solution may be utilized as long as it does not interact with the rhenium carbonyl and cause decomposition of same. Obviously, the organic solution should be anhydrous in order to avoid detrimental interaction of water with the rhenium carbonyl complex. Suitable solvents are any of the commonly available organic solvents such as one of the available ethers, alcohols, ketones, aldehydes, paraffins, naphthenes and aromatic hydrocarbons, for example, acetone, acetyl acetone, benzaldehyde, pentane, hexane, carbon tetrachloride, methyl isopropyl ketone, benzene, n-butylether, diethyl ether, ethylene glycol, methyl isobutyl ketone, diisobutyl ketone and the like organic solvents. Best results are ordinarily obtained when the solvent is acetone; consequently, the preferred impregnation solution is rhenium carbonyl dissolved in anhydrous acetone. The rhenium carbonyl complex suitable for use in the present invention may be either the pure rhenium carbonyl itself or a substituted rhenium carbonyl such as the tin-containing complexes like $ClSn[Re(CO)_5]_3$ mentioned previously or the rhenium carbonyl halides including the chlorides, bromides, and iodides and the like substituted rhenium carbonyl complexes. After impregnation of the carrier material with the rhenium carbonyl component, it is important that the solvent be removed or evaporated from the catalyst prior to decomposition of the rhenium carbonyl component by means of the hereinafter described pyrolysis step. The reason for removal of the solvent is that I believe that the presence of organic materials such as hydrocarbons or derivatives of hydrocarbons during the rhenium carbonyl pyrolysis step is highly detrimental to the synergistic interaction associated with the present invention. This solvent is removed by subjecting the rhenium carbonyl impregnated carrier material to a temperature of about 100° F. to about 250° F. in the presence of an inert gas or under a vacuum condition until no further substantial amount of solvent is observed to come off the impregnated material. In the preferred case where acetone is used as the impregnation solvent, this drying of the impregnated carrier material typically takes about one half hour at a temperature of about 225° F. under moderate vacuum conditions.

After the rhenium carbonyl component is incorporated into the platinum group metal-containing porous carrier material, the resulting composite is, pursuant to the present invention, subjected to pyrolysis conditions designed to decompose substantially all of the rhenium carbonyl material, without oxidizing either the platinum group component or the decomposed rhenium carbonyl component. This step is preferably conducted in an atmosphere which is substantially inert to the rhenium carbonyl such as in a nitrogen or noble gas-containing atmosphere. Preferably this pyrolysis step takes place in the presence of a substantially pure and dry hydrogen stream. It is of course within the scope of the present invention to conduct the pyrolysis step under vacuum conditions. It is much preferred to conduct this step in the substantial absence of free oxygen and substances that could yield free oxygen under the conditions selected. Likewise it is clear that best results are obtained when this step is performed in the total absence of water and of hydrocarbons and other organic materials. I have obtained best results in pyrolyzing rhenium carbonyl while using an anhydrous hydrogen stream at pyrolysis conditions including a temperature of about 300° F. to about 900° F. or more, preferably about 400° F. to about 750° F., a gas hourly space velocity of about 250 to about 1500 hr.$^{-1}$ for a period of about 0.5 to about 5 or more hours until no further evolution of carbon monoxide is noted. After the rhenium carbonyl component has been pyrolyzed, it is a much preferred practice to maintain the resulting catalytic composite in an inert environment (i.e. a nitrogen or the like inert gas blanket) until the catalyst is loaded into a reaction zone for use in the conversion of hydrocarbons.

It is essential to incorporate a halogen component into the trimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g., as the chloride). This combined halogen may be either fluorine, chlorine, iodine, bromine, or mixtures thereof. Of these, fluorine and particularly chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation or incorporation of the latter with the platinum group metal and tin components, for example, through the utilization of a mixture of chloroplatinic acid and hydrogen chloride. In another situation, the alumina hydrosol which is typically utilized to form a preferred alumina carrier material may contain halogen and thus contribute at least a portion of the halogen component to the final composite. The halogen will be typically combined with the carrier material in an amount sufficient to result in a final composite that contains about 0.1 to about 10% and preferably about 1 to about 5%, by weight, of halogen, calculated on an elemental basis. It is to be understood that the specified level of halogen component in the instant catalyst can be achieved or maintained during use in the present isomerization process by continuously or periodically adding to the reaction zone a decomposable halogen-containing compound such as an organic chloride (e.g., ethylene dichloride, carbon tetrachloride, t-butyl chloride) in an amount of about 1 to 100 wt. ppm. of the hydrocarbon feed, and preferably about 1 to 10 wt. ppm.

An optional ingredient for the attenuated superactive multimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith—for example, an embodiment wherein the hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, this optional ingredient can be incorporated into the composite of the present invention by any of the conventional methods for adding metallic halides of this type and either prior to or after the rhenium carbonyl reagent is added thereto; however, best results are ordinarily obtained when the metallic halide is sublimed onto the surface of the carrier material after the rhenium is added thereto according to the preferred method disclosed in U.S. Pat. No. 2,999,074. The component can generally be utilized in any amount which is catalytically effective, with a value selected from the range of about 1 to about 100 wt.% of the carrier material generally being preferred.

In the preferred method, wherein the catalytic composite is impregnated with a Friedel-Crafts metal halide component, the presence of chemically combined hydroxyl groups in the refractory inorganic oxide allows a reaction to occur between the Friedel-Crafts metal halide and the hydroxyl group of the carrier material. For example, aluminum chloride reacts with the hydroxyl groups of the preferred alumina carrier material to yield Al-O-AlCl$_2$ active centers which enhance the catalytic behavior of the composite. Since chloride ions and hydroxyl ions occupy similar sites on the carrier surface, more hydroxyl sites will be available for possible interaction with the Friedel-Crafts metal halide when the chloride population of the carrier sites is low. Therefore, potentially more active Friedel-Crafts type versions of the catalyst will be obtained when the chloride content of the carrier material is in the low range of the 0.1 to 10 wt.% range. Some halogen must be present on the carrier material at all times, however, to maintain proper dispersion of the other active elements.

The Friedel-Crafts metal halide may be impregnated onto the calcined composite containing combined hydroxyl groups by the sublimation of the Friedel-Crafts metal halide onto the calcined composite under conditions such that the sublimed Friedel-Crafts metal halide is combined with the hydroxyl groups of the calcined composite. This reaction is typically accompanied by the elimination of about 0.5 to about 2.0 moles of hydrogen chloride per mole of Friedel-Crafts metal halide reacted with the carrier material. For example, in the case of subliming aluminum chloride, which sublimes at about 184° C., suitable impregnation temperatures range from about 190° C. to about 700° C., with a preferably range being between about 200° C. and about 600° C. In any event, the sublimation temperature must be selected so as to preclude the alteration of the oxidation states of metal components. The sublimation can be conducted at atmospheric pressure or under increased pressure and in the presence or absence of diluent gases such as hydrogen or light paraffinic hydrocarbons or both. The impregnation of the Friedel-Crafts metal halide may be conducted batch wise, but a preferred method for impregnating the calcined composite is to pass sublimed $AlCl_3$ vapors, in admixture with a carrier gas such as hydrogen, through a catalyst bed. This method both continuously deposits and reacts the aluminum chloride and also removes the evolved HCl.

The amount of Friedel-Crafts metal halide combined with the catalytic composite may range from about 1 wt.% up to about 100 wt.% of the Friedel-Crafts metal halide-free, catalytic composite as abovementioned. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of $AlCl_3$, temperatures of about 400° C. to about 600° C., and times of from about 1 to about 48 hours are sufficient.

The resulting catalytic composite is preferably maintained in a sulfur-free state during its preparation and use. Once the catalyst has been exposed to hydrocarbon for a sufficient period of time to lay down a protective layer of carbon or coke on the catalyst, the sulfur sensitivity of the catalyst changes rather markedly and the presence of small amounts of sulfur can be tolerated. Thus, contact of fresh catalyst with sulfur can seriously damage the catalyst and jeopardize the superior performance characteristics of the catalyst. However, once a protective layer of carbon is established on the catalyst, the sulfur deactivation effect is less permanent and the sulfur can be purged from the catalyst by exposure to a sulfur-free hydrogen stream at 425° C. to 460° C.

According to the process of the present invention, an isomerizable hydrocarbon charge stock, preferably in admixture with hydrogen, is contacted with a catalyst of the type hereinbefore described in a hydrocarbon isomerization zone. Contacting may be effected using the catalyst in a fixed bed system, a moving bed system, a fluidized bed system, or in a batch type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of the catalyst type previously characterized. The conversion zone may be one or more separate reactors with suitable means therebetween to insure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst, with best results obtained in a vapor phase.

The process of this invention, utilizing the catalyst described above for isomerizing isomerizable olefinic or saturated hydrocarbons, is preferably effected in a continuous down-flow fixed bed system. One preferred method is to pass the hydrocarbons continuously, preferably commingled with about 0.1 to about 10 moles or more of hydrogen per mole of hydrocarbon, to an isomerization reaction zone containing the catalyst, and to maintain the zone at proper isomerization conditions such as a temperature in the range of about 0° C. to about 425° C. or more and a pressure of about atmospheric to about 100 atmospheres or more. The hydrocarbon is passed over the catalyst at a liquid hourly space velocity (defined as volume of liquid hydrocarbon passed per hour per volume of catalyst) of from about 0.1 to about 10 hr.$^{-1}$ or more. In addition, diluents such as argon, nitrogen, etc., may be present. The isomerized product is continuously withdrawn, separated from the reactor effluent, and recovered by conventional means such as fractional distillation, while the unreacted starting material may be recycled to form a portion of the feedstock.

The process of this invention for isomerizing an isomerizable alkylaromatic hydrocarbon is preferably effected by contacting the alkylaromatic, in a reaction zone containing the hereinbefore described catalyst, with a fixed catalyst bed by passing the hydrocarbon in a down-flow fashion through the bed, while maintaining the zone at proper alkylaromatic isomerization conditions such as a temperature in the range from about 0° C. to about 600° C. or more, and a pressure of atmospheric to about 100 atmospheres or more. The hydrocarbon is passed, preferably, in admixture with hydrogen at a hydrogen to hydrocarbon mole ratio of about 0.5:1 to about 20:1 or more, and at a liquid hourly hydrocarbon space velocity of about 0.1 to about 20 hr.$^{-1}$ or more. Other inert diluents such as nitrogen, argon, etc., may be present. The isomerized product is continuously withdrawn, separated from the reactor effluent by conventional means including fractional distillation or crystallization, and recovered.

The following illustrative embodiments are given to illustrate further the preparation of the multimetallic catalytic composite utilized in the process of the present invention and the employment of the catalyst in isomerization of hydrocarbons. It is to be understood that the examples are illustrative rather than restrictive.

ILLUSTRATIVE EMBODIMENT I

This example demonstrates a particularly good method of preparing the preferred catalytic composite utilized in the process of the present invention.

A sulfur-free tin- and chloride-containing alumina carrier material comprising 1/16-inch spheres was prepared by: forming an aluminum hydroxy chloride sol by dissolving substantially pure aluminum pellets in a hydrochloric acid solution, thoroughly mixing stannic chloride with the resulting sol in an amount selected to result in a final catalyst containing about 0.2 wt.% tin, adding hexamethylenetetramine to the resulting tin-containing alumina sol, gelling the resulting solution by dropping it into an oil bath to form spherical particles of a tin-containing alumina hydrogel, aging and washing the resulting particles and finally drying and calcining the aged and washed particles to form spherical particles of gamma-alumina having a tin component uniformly dispersed therein and containing, on an elemental basis, about 0.2 wt.% tin and about 0.3 wt.% combined chloride. Additional details as to this method of preparing the preferred gamma-alumina carrier material are given in the teachings of U.S. Pat. No. 2,620,314.

An aqueous impregnation solution containing chloroplatinic acid and hydrogen chloride was then prepared. The sulfur-free, tin-containing alumina carrier material particles were thereafter admixed with this impregnation solution. The amounts of the metallic reagents contained in this impregnation solution were calculated to result in a final composite containing, on an elemental basis, about 0.375 wt.% platinum. In order to insure uniform dispersion of the platinum component throughout the carrier material, the amount of hydrogen chloride used in this impregnation solution was about 2 wt.% of the alumina particles. This impregnation step was performed by adding the carrier material particles to the impregnation mixture with constant agitation. In addition, the volume of the solution was approximately the same as the bulk volume of the alumina carrier material particles so that all of the particles were immersed in the impregnation solution. The impregnation mixture was maintained in contact with the carrier material particles for a period of about $\frac{1}{2}$ to about 3 hours at a temperature of about 70° F. Thereafter, the temperature of the impregnation mixture was raised to about 225° F. and the excess solution was evaporated in a period of about 1 hour. The resulting dried impregnated particles were then subjected to an oxidation treatment in a dry air stream at a temperature of about 975° F. and a GHSV of about 500 hr.$^{-1}$ for about $\frac{1}{2}$ hour. This oxidation step was designed to convert substantially all of the platinum and tin ingredients to the corresponding oxide forms. The resulting oxidized spheres were subsequently contacted in a halogen-treating step with an air stream containing $H_2O$ and HCl in a mole ratio of about 30:1 for about 2 hours at 975° F. and a GHSV of about 500 hr.$^{-1}$ in order to adjust the halogen content of the catalyst particles to a value of about 1 wt.%. The halogen-treated spheres were thereafter subjected to a second oxidation step with a dry air stream at 975° F. and a GHSV of 500 hr.$^{-1}$ for an additional period of about $\frac{1}{2}$ hour.

The resulting oxidized, halogen-treated, platinum- and tin-containing carrier material particles were then subjected to a dry reduction treatment designed to reduce substantially all of the platinum component to the elemental state and to maintain a uniform dispersion of this component in the carrier material. This reduction step was accomplished by contacting the particles with a hydrocarbon-free, dry hydrogen stream containing less than 5 vol. ppm. $H_2O$ at a temperature of about 1050° F., a pressure slightly above atmospheric, a flow rate of hydrogen through the particles corresponding to a GHSV of about 400 hr.$^{-1}$ and for a period of about one hour.

Rhenium carbonyl complex, $Re_2(CO)_{10}$, was thereafter dissolved in an anhydrous acetone solvent in order to prepare the rhenium carbonyl solution which was used as the vehicle for reacting rhenium carbonyl with the carrier material containing the uniformly dispersed platinum and tin. The amount of this complex used was selected to result in a finished catalyst containing about 0.375 wt.% rhenium derived from rhenium carbonyl. The resulting rhenium carbonyl solution was then contacted under appropriate impregnation conditions with the reduced, platinum- and tin-containing alumina carrier material resulting from the previously described reduction step. The impregnation conditions utilized were: a contact time of about $\frac{1}{2}$ to about 3 hours, a temperature of about 70° F. and a pressure of about atmospheric. It is important to note that this impregnation step was conducted under a nitrogen blanket so that oxygen was excluded from the environment and also this step was performed under anhydrous conditions. Thereafter the acetone solvent was removed under flowing nitrogen at a temperature of about 175° F. for a period of about one hour. The resulting dry rhenium-carbonyl-impregnated particles were then subjected to a pyrolysis step designed to decompose the rhenium carbonyl compound. This step involved subjecting the rhenium carbonyl impregnated particles to a flowing hydrogen stream at a first temperature of about 230° F. for about $\frac{1}{2}$ hour at a GHSV of about 600 hr.$^{-1}$ and at atmospheric pressure. Thereafter in the second portion of the pyrolysis step, the temperature of the impregnated particles was raised to about 575° F. for an additional interval of about one hour until the evolution of CO was no longer evident. The resulting catalyst was then maintained under a nitrogen blanket until it was used.

A sample of the resulting pyrolyzed rhenium-carbonyl-, tin- and platinum-containing catalytic composite contained, on an elemental basis, about 0.375 wt.% platinum, about 0.375 wt.% rhenium derived from the carbonyl, about 0.2 wt.% tin and about 1.0 wt.% chlorine. For this catalyst the atomic ratio of tin to platinum was about 0.88:1 and the atomic ratio of rhenium to platinum was about 1.05:1

ILLUSTRATIVE EMBODIMENT II

A portion of the spherical multimetallic catalyst particles produced by the method described in Illustrative Embodiment I is loaded into a continuous, fixed bed isomerization plant of conventional design. The charge stock, containing on a weight percent basis, 20.0% ethylbenzene, 10.0% para-xylene, 50.0% meta-xylene, and 20.0% ortho-xylene is commingled with about 8 moles of hydrogen per mole of hydrocarbon, heated to 400° C., and continuously charged at 4.0 hr.$^{-1}$ liquid hourly space velocity (LHSV) to the reactor which is maintained at a pressure of 30 atm, absolute. The resulting product evidences essentially equilibrium conversion to para-xylene with only insignificant amounts of cracked products thus indicating an efficient alkylaromatic isomerization catalyst.

ILLUSTRATIVE EMBODIMENT III

A portion of the catalyst produced by the method of Illustrative Embodiment I is placed in a continuous flow, fixed bed isomerization plant of conventional design as utilized in Illustrative Embodiment II. Substantially pure meta-xylene is used as a charge stock. The charge stock is commingled with about 8 moles of hydrogen per mole of hydrocarbon, heated to about 390° C., and continuously charged to the reactor which is maintained at a pressure of about 21 atm. Substantial conversion of meta-xylene to para-xylene is obtained.

ILLUSTRATIVE EMBODIMENT IV

A catalyst identical to that produced in Illustrative Embodiment I but containing only 0.40 wt.% combined chloride is used to isomerize 1-butene in an appropriate isomerization reactor, at a reactor pressure of about 35 atm and a reactor temperature of about 140° C. Substantial conversion to 2-butene is observed.

ILLUSTRATIVE EMBODIMENT V

The same catalyst as utilized in Illustrative Embodiment IV is charged to an appropriate, continuous isomerization reactor of conventional design maintained at a reactor pressure of about 70 atm and a reactor temperature of about 180° C. and 3-methyl-1-butene is continuously passed to this reactor with substantial conversion to 2-methyl-2-1-butene being observed.

ILLUSTRATIVE EMBODIMENT VI

A catalyst, identical to that catalyst produced in Illustrative Embodiment I except that the gamma-alumina particles are contacted with hydrogen fluoride to provide a 2.9 wt.% combined fluoride content in the catalyst, is placed in an appropriate continuous isomerization reactor of conventional design maintained at a reactor pressure of about 21 atm psig. and a reactor temperature of about 200° C. Normal hexane is continuously charged to the reactor and substantial conversion to 2,2-dimethylbutane, 2,3-dimethylbutane, 2-methylpentane, and 3-methylpentane is observed.

ILLUSTRATIVE EMBODIMENT VII

A portion of the catalyst prepared in Illustrative Embodiment I is placed in an appropriate continuous isomerization apparatus and used to isomerize normal butane at a reactor pressure of 21 psig, a 0.5 hydrogen to hydrocarbon mole ratio, a 1.0 liquid hourly space velocity, and a reactor temperature of 230° C. Substantial conversion of normal butane to isobutane is observed.

ILLUSTRATIVE EMBODIMENT VIII

A portion of the catalyst prepared in Illustrative Embodiment I is placed in an appropriate continuous isomerization reactor maintained at a reactor temperature of about 210° C. and a reactor pressure of about 18 atm. Methylcyclopentane is continuously passed to this reactor with a substantial conversion to cyclohexane being observed.

ILLUSTRATIVE EMBODIMENT IX

A portion of the catalyst prepared in Illustrative Embodiment I is placed in a glass lined, rotating autoclave with anhydrous aluminum chloride. Three weights of $AlCl_3$ are added for each four weights of catalyst particles. The autoclave is sealed, evacuated, then pressured with $H_2$ to 3 atm, absolute. The autoclave is heated to 300° C. for two hours, with rotation. The catalyst particles experienced a weight gain of 15 wt.%.

ILLUSTRATIVE EMBODIMENT X

Catalyst prepared in Illustrative Embodiment IX is tested for isomerization of normal butane at a 0.5 $H_2$ to hydrocarbon ratio, 1.0 LHSV, and reactor temperature of 150° C. Substantial conversion of normal butane to isobutane is observed.

ILLUSTRATIVE EMBODIMENT XI

About 100 g of the catalyst prepared in Illustrative Embodiment I is placed in a vertical Pyrex tube with a bed of 30 g of $AlCl_3$ on top. $H_2$ at 250° C. and gas hourly space velocity of 250 is passed over the bed until complete sublimation of $AlCl_3$ is observed. The temperature is then increased to 300° C. for 30 minutes. The catalyst particles are then cooled under $N_2$ gas flow.

ILLUSTRATIVE EMBODIMENT XII

Catalyst prepared in Illustrative Embodiment XI is tested as disclosed in Illustrative Embodiment X. Substantial conversion of normal butane to isobutane is observed.

The foregoing specification, and particularly the illustrative embodiments indicate the method by which the present invention is effected, and the benefits afforded through the utilization thereof.

I claim:

1. A catalytic composite comprising a combination of a catalytically effective amount of a pyrolyzed rhenium carbonyl component with a porous carrier material containing a uniform dispersion of catalytically effective amounts of a platinum group component, which is maintained in the elemental metallic state during the incorporation and pyrolysis of the rhenium carbonyl component, of a tin component, of a halogen component and of about 1 to about 100 wt. % of a Friedel-Crafts metal halide calculated on a Friedel-Crafts metal halide-free basis.

2. The catalyst of claim 1 wherein the platinum group metal is platinum.

3. The catalyst of claim 1 wherein the platinum group metal is palladium.

4. The catalyst of claim 1 wherein the porous carrier material is a refractory inorganic oxide.

5. The catalyst of claim 1 wherein the refractory inorganic oxide is alumina.

6. The catalyst of claim 1 wherein the halogen is combined chloride.

7. The catalyst of claim 1 containing 0.01 to about 2 wt. % platinum group metal, about 0.05 to about 5 wt. % tin, about 0.01 to about 5 wt. % rhenium and about 0.5 to about 1.5 wt. % halogen.

8. The catalyst of claim 1 wherein the Friedel-Crafts metal halide is aluminum chloride.

* * * * *

UNITED STATES PATENT AND TRADEMARK OFFICE
CERTIFICATE OF CORRECTION

PATENT NO. : 4,333,856
DATED : 6-8-82
INVENTOR(S) : George J. Antos

It is certified that error appears in the above—identified patent and that said Letters Patent are hereby corrected as shown below:

>Cover page, lefthand column, the sentence "The portion of the term of this patent subsequent to Jul. 23, 1998, has been disclaimed." should read --The portion of the term of this patent subsequent to Jan. 26, 1999, has been disclaimed.--

Signed and Sealed this

Third Day of August 1982

[SEAL]

Attest:

*Attesting Officer*

GERALD J. MOSSINGHOFF

*Commissioner of Patents and Trademarks*